United States Patent [19]

Cone, Jr.

[11] 4,018,649

[45] Apr. 19, 1977

[54] PROCESS FOR CONTROL OF CELL DIVISION

[76] Inventor: Clarence D. Cone, Jr., 104 Harbour Drive, Yorktown, Va. 23490

[22] Filed: Oct. 17, 1975

[21] Appl. No.: 623,238

Related U.S. Application Data

[63] Continuation of Ser. No. 314,656, Dec. 13, 1972, abandoned, which is a continuation of Ser. No. 125,235, March 17, 1971, abandoned.

[52] U.S. Cl. .................................................. 195/1.8
[51] Int. Cl.² .......................................... C12K 9/00
[58] Field of Search ..................................... 195/1.8

[56] References Cited

OTHER PUBLICATIONS

Cone–N.Y., Acad. Sci. Transactions, vol. 31, Apr. 1969, pp. 404–427.
Cone–Oncology, vol. 24, (1970), pp. 438–470.
Cone–J. Theoretical Biology, Jan. 1971, pp. 151–194.
Lubin–The Cellular Functions of Membrane Transport, 1964, pp. 193–211.
Whitfield et al.–Experimental Cell Research, vol. 35, 1964, pp. 207–210.
Owens et al., Federation Proceedings, vol. 15, 1956, p. 140.
Orr et al.–Proc. Nat. Acad. Sci., U.S.A., vol. 69, Jan. 1972, pp. 243–247.

*Primary Examiner*—Sam Rosen
*Attorney, Agent, or Firm*—Howard J. Osborn; John R. Manning

[57] ABSTRACT

A method of controlling mitosis of biological cells by inducing a change in the intracellular ionic hierarchy accompanying the cellular electrical transmembrane potential difference ($E_m$) of the cells. The ionic hierarchy may be varied by imposing changes on the relative concentrations of $Na^+$, $K^+$, and $Cl^-$, or by directly imposed changes of the physical $E_m$ level across the cell surface.

10 Claims, 5 Drawing Figures

PROCESS FOR CONTROL OF CELL DIVISION

ORIGIN OF THE INVENTION

The invention described herein was made by an employee of the United States Government and may be manufactured and used by or for the Government for governmental purposes without the payment of any royalties thereon or therefor.

CROSS-REFERENCES TO RELATED APPLICATIONS

This application is a streamlined continuation of application Ser. No. 314,656, filed Dec. 13, 1972, which is a streamlined continuation of application Ser. No. 125,235, filed Mar. 17, 1971, both of which are now abandoned.

BACKGROUND OF THE INVENTION

Many agents have been found which will either block or stimulate cell division. However, generally speaking, these agents will not both block and/or stimulate cell division. Most of the known blocking agents are of a chemical nature quite foreign to the natural metabolic regime of the cell and often induce highly abnormal metabolic conditions leading to cell death or permanent aberrancies of the cell. These types of agents are also generally nonspecific and block division indiscriminately in all cell types. The blockage usually occurs through highly abnormal mechanisms and at abnormal places in the cell's metabolic cycle. The few known mitotic stimulatory agents are generally highly specific in the cell types which they activate, and thus are quite restricted in their usefulness.

SUMMARY OF THE INVENTION

In view of the difficulties in using the above-mentioned chemical agents, a need exists for a process which can be used to both stimulate and block cell division, but in a reversible manner which will be relatively natural in its action and will not introduce grossly abnormal changes in cellular metabolism and function. It is also a purpose of the invention to provide a method which will offer the potential for selective or specific blockage of mitosis which can be applied to specific cell division problems. Generally, this is accomplished in the present invention by controlling the intracellular inorganic ion hierarchy of the particular cells involved. Control is accomplished by changing the absolute and relative concentrations of the $Na^+$, $K^+$, and $Cl^-$ which accompany various levels of the cellular electrical transmembrane potential difference ($E_m$). It has been found that this control exerts a pronounced effect over the essential prerequisite metabolic events required for cell division.

DESCRIPTION OF PREFERRED EMBODIMENT OF THE INVENTION

Figure 1:
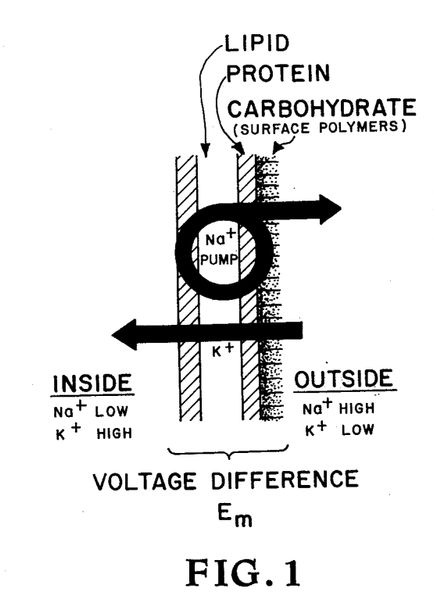
FIG. 1 is a diagramatic view showing the common membrane transport theory.

The essential principle of the mitotic control process of the present invention consists in inducing the cell-type of interest to assume an intracellular concentraton hierarchy of $Na^+$, $K^+$, and $Cl$ corresponding to a large negative $E_m$ level (e.g., −70 to −90mV) to block division, and a small negative $E_m$ level (e.g., −10 to −20mV) to stimulate active proliferation. $E_m$ is the symbolic designation for the cellular electrical transmembrane potential difference which is measured in millivolts, relative to the potential of the external culture medium or extracellular bathing fluid. The required intracellular concentration hierarchy corresponding to the $E_m$ limits is determinable by use of common membrane transport theory wherein $Na^+$ is the actively transported ion ($K^+$ and $Cl^-$ being considered passively distributed), or else estimated from values obtained by actual experimental measurements of the intracellular concentrations of $Na^+$, $K^+$ and $Cl^-$ in cells having known $E_m$ levels. FIG. 1 illustrates the common membrane transport theory in a normal biological cell. Such a cell possesses a substantial degree of negative electrical charge produced by active pumping of positive sodium ions out of the cell. The removal of sodium ions generates a substantial electrical voltage $E_m$ across the surface membrane. This voltage can be accurately measured by inserting ultramicro electrodes into the cells, and serves as a convenient indication of the degree to which the ionic concentrations, primarily those of $Na^+$ and potassium $K^+$, differ between the inside and outside of the cell. The imposed intracellular ionic concentration hierarchy for either blockage or stimulation of mitosis must be held for a time sufficient for intracellular metabolic circuits to adjust and respond to the new ionic environment, and then held for such additional time as mitotic control is required. In particular, for stimulation of mitosis, the cell must be held in the equivalent $E_m$ state for a period corresponding to the normal $G_1$ and $S$ periods of the generation cycle for the cell under consideration before mitosis can begin.

There are numerous ways in which the essential ionic concentration hierarchies can be obtained, the precise manner used not being, however, of primary importance or relevance as far as the essential principle of the invention is concerned. One method which has been used and that has practical application for obtaining the desired intracellular ionic hierarchy is to surround the cell or cells of interest with a physiological solution entirely equivalent to that normally surrounding the cell except the the concentrations of $Na^+$, $K^+$ and $Cl^-$ are changed such that upon attainment of diffusional equilibrium, the diffusion gradients existing across the cell membrane will force the intracellular ionic concentrations of $Na^+$, $K^+$ and $Cl^-$ to assume the metabolically effective values required for mitosis blockage or stimulation. Of course, use of any chemical or physical means which would cause actual alteration of the physically existing $E_m$ level of the cell (and its associated ion concentration hierarchy) to a high or a low negative value so as to block or stimulate mitosis, respectively, would serve to achieve the necessary change in the intracellular ion hierarchy of $Na^+$, $K^+$, and $Cl^-$ to effect the desired mitotic control. One other such control is by changing the surface ionic permeability of the cells. The essential feature in the application of these techniques is that the necessary intracellular concentration hierarchy of $Na^+$, $K^+$, and $Cl^-$ be attained without overt damage to the cells.

Referring to the specific examples which illustrated that cell divisions may be controlled by varying $E_m$ level of the cells, all examples were performed with naturally synchronized Chinese hamster cells in monolayer culture.

EXAMPLE I

The basic concept of ionic control of cell division was tested in a preliminary experiment as follows. Chinese hamster cells growing in monolayer culture in F-10 culture medium, and actively proliferating, had their F-10 medium replaced with a culture medium identical to F-10 but in which the $Na^+$ concentration was reduced to that existing intracellulary in nerve cells (where $E_m = -70mV$ and no mitosis occurs), a value equal to approximately 20 $\mu$mol/ml. Shortly after change to this low-$Na^+$ medium, all cell division ceased, and the cells remained mitotically quiescent as long as they were maintained in this medium (a period of several normal cell cycles). Soon after replacement of this low-$Na^+$ medium with the normal F-10 medium (wherein the $Na^+$ level is approximately 145 $\mu$mol/ml), rapid mitotic proliferation was resumed in the culture.

In Examples II through VI synchronization was accomplished by the metaphase shake-off technique which generally yielded test cell populations consisting essentially of 85 to 90 percent metaphase cells.

The stock cultures and example controls were maintained in F-10 medium (without added $Ca^{++}$) supplemented with 10 percent calf serum and 5 percent fetal calf serum. F-10 medium is the standard growth medium used in the culture of the CHO cell line. Since the generation cycle period of cells may vary considerably with the culture medium prepared from different lots of serum, all experiments of the present study were performed using the same serum lot.

The primary test medium, designated $HEM_{100}$ ("high potential medium") was designed to produce intracellular osmotic conditions and concentrations of $Na^+$, $K^+$, and $Cl^-$ approximating those of cells having an $E_m$ level equal to $-90mV$. This $HEM_{100}$ formulation was based on the assumption that at equilibrium, the intracellular concentration of $Na^+$, $K^+$, and $Cl^-$ in cells maintained in this medium would be essentially the same as in the medium itself, since the basic $E_m$ level of the cells in vitro is so small. The $HEM_{100}$ was made by substituting for the usual NaCl, KCl, and $NaHCO_3$ components of the normal F-10 medium, the prope amounts of $Na_2SO_4$, $K_2SO_4$, KCl, $KHCO_3$, and sucrose to yield required osmolarity and $Na^+$, $K^+$, and $Cl^-$ concentrations, with due allowance for the $Na^+$ and $K^+$ content of the serum used. In determining the osmotic balance, $SO_4$ was assumed to be impermeable to the cell.

To obtain test media approximating other $E_m$ levels (i.e., less than $-90mV$), the primary $HEM_{100}$ was diluted with increasing amounts of normal F-10 medium. This medium series was designated $HEM_{xx}$, where the subscript expresses the percentage of $HEM_{100}$ in the particular test medium, for example, $HEM_{55}$ consists of 55 percent $HEM_{100}$ and 45 percent normal F-10 medium. Thus, as the test medium varies from 100 to 0 percent $HEM_{100}$, the corresponding ionically simulated $E_m$ varies from $-90mV$ to $-10mV$.

In reality, it was not possible to make up $HEM_{100}$ medium per se since the $Na^+$ contribution of the serum component used was itself in excess of the required 12 $\mu$mol/ml for a $-90$ mV simulation. The highest $E_m$ simulation medium actually obtainable was $HEM_{89}$; all concentrations of the $E_m$ simulation series herein are, however, expressed in terms of the equivalent dilution of $HEM_{100}$ with normal F-10, although actually prepared by the dilution of $HEM_{89}$. Final $Na^+$ and $K^+$ concentrations in the test media were verified by direct atomic absorptions spectrographic analysis.

EXAMPLE II

An initial test was conducted to determine the minimum $HEM_{100}$ concentration (i.e., $E_m$ level) which completely blocks division in the cells. Pooled, synchronized cells obtained by the shake-off method mentioned above, where chill accumlated in F-10 medium for a given test and innoculated into plastic culture flasks with F-10 at 37° C. Fifty minutes were allowed for the cells so complete initial division and attach to the culture plate. The end of this period was designated time zero ($t=0$) and corresponds to very late telophase in the cell cycle. During the settling period, the open flasks were exposed to a 5 percent $CO_2$ atmosphere. The test medium concentrations studies ranged from $HEM_0$ (i.e., the normal F-10 control) to $HEM_{89}$. Duplicate test flasks were used for each medium concentration. All cells for a given test were taken from the same shake-off population. Cell surface densities in the test flasks were sufficiently sparse and uniform to preclude and mitotic ihibitional effects due to confluency up to intervals of several cell cycle times, T. At confluency, cell surface density is approximately 1800 cells per millimeters$^2$. At $t=0$, the F-10 of the test flasks were replaced with test medium, following two washings with test medium, and the cells incubated at 37° C. Viable-cell counts were made visually within specific ruled areas of the culture flasks at $t=0$, and at 24-hour intervals for 96 hours, or until confluence occurred. The ruled areas of each flask contained a total of approximately 500 initial cells ($t=0$). The minimum HEM concentration required for complete mitotic blockage was found to be $HEM_{85}$ ($-70mV$); this medium was consequently used for all subsequent tests. The pH was monitored throughout the experimental period by observation of the medium indicator color; cell culture pH was maintained between 6.8 and 7.0.

EXAMPLE III

The effects of $HEM_{85}$ on mitotic activity were determined on naturally synchronized cells using exactly the same procedures outlined above for the preliminary test, only cell counts were made at 2-hour intervals from $t=0$ to $t=33$ hours. At $t=33$ hours, the test medium was replaced with normal F-10 and the cell counts continued for an additional 20-hour period to determine if mitosis recovery occurred.

EXAMPLE IV

A long-term test was conducted similar to the others, only the cells were maintained continuously in the $HEM_{85}$ medium for 120 hours (6T) with periodic counts of the viable cell numbers, following which the $HEM_{85}$ was replaced with F-10 and the culture observed for resumption of mitotic activity.

EXAMPLE V

A comparison long-term test was run similar to the others using F-10 medium containing 0.40 mg/ml of 5-aminouracil. The minimum concentration found to block all mitosis in cells to ascertain the relative effects on the cells of mitotic blockage by $HEM_{85}$ and by a commonly used exogenous chemical blocking agent.

EXAMPLE VI

The effects of $HEM_{85}$ on DNA synthesis activity were determined by pulse labelling with $^3H$-thymidine. The tests were conducted with cell samples prepared in exactly the same manner as those above for both short and long term mitotic blockage and recovery tests; the test cells were incubated, however, on plastic slides (made from plastic flask bottoms) immersed in $HEM_{85}$. Sample slides were removed periodically from the $HEM_{85}$ and incubated for 15 minutes in $HEM_{85}$ containing 0.5 $\mu$ M/ml of $^3H$-thymidine (activity equal to 15 $\mu$ c/mM) following which they were washed, fixed (3:1 ethonol:acetic acid), dried, coated with NTB-3 liquid emulsion (Kodak), and exposed for 12.2 days. Time of fixation was taken as the test sample time (relative to time zero). Following development in Dektol (Kodak), nuculear straining was performed with 0.25 percent toluidine blue. DNA synthesis activity was determined by scoring the fractions of cells with labelled nuclei corresponding to each sample time, using 1,000 randomly selected cells per sample slide.

RESULTS

The results of Example I support fully the concept that the intracellular ionic hierarchy is able to control cell division. The low-$Na^+$ medium apparently caused an efflux of $Na^+$ from the cells and made the intracellular conditions similar (in respect to $Na^+$) to those which would have existed if the cell had actually been able to physically generate an electrical potential ($E_m$) of $-70mV$ by pumping out $Na^+$. This experiment constituted the first and fundamental experimental verification of the concept of ionic control of cell division.

Figure 2:
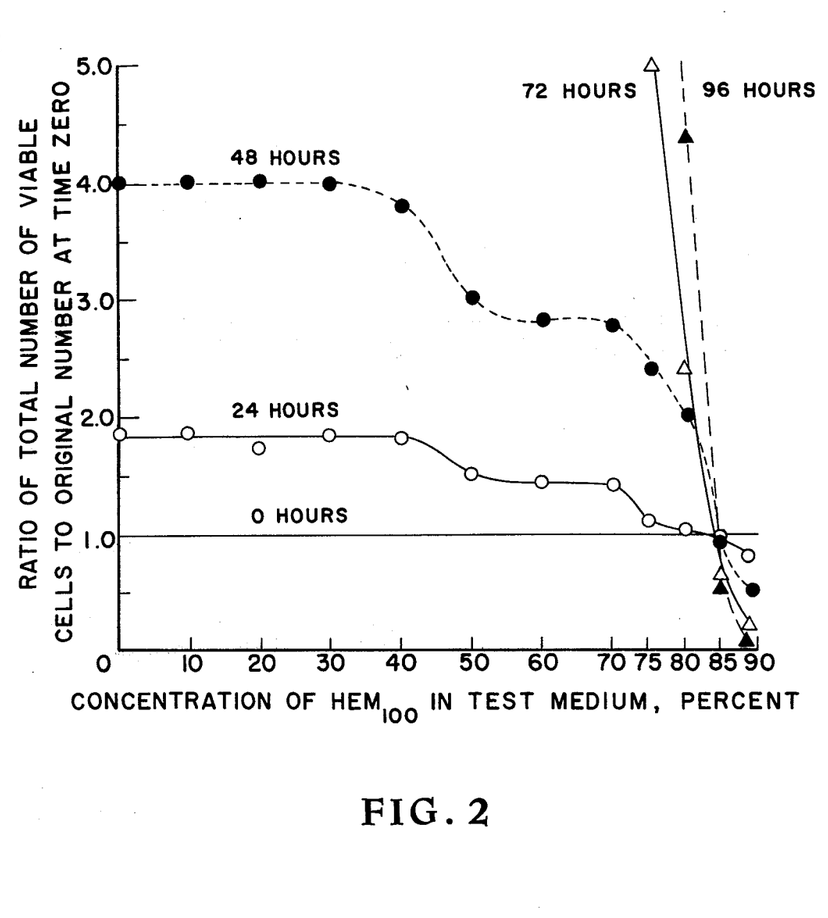
FIG. 2 is a graph showing the effect of simulated ($E_m$) level ($HEM_{100}$ test medium) on mitotic activity of naturally synchronized mammalian somatic cells, as determined at 24-hour intervals.

The effects of simulated $E_m$ level on the mitotic activity of naturally synchronized cells over a 96-hour period are shown in FIG. 2 (Example II). Immediate mitotic suppression (i.e., within 24 hours) began at about $HEM_{45}$ ($\sim-36mV$) and reached the condition of complete arrest at $HEM_{85}$ ($\sim-70mV$). This latter level is the same as that maintained in vivo by nondividing eurons. Above $HEM_{84}$, cell division is completely arrested and cell death slowly reduces the population at $HEM_{85}$ and more rapidly at $HEM_{89}$. By direct observation, no cell death above the normal control (i.e., $HEM_0$ or F-10) value of 4 percent of a given population for 24 hours occurred for $HEM_{80}$ and below during the 96-hour period. The crossover point between net proliferation and net population decrease occurs for all time periods in the vicinity of $HEM_{84}$; at this $E_m$ level, therefore the small fraction of cells which die in each time period is exactly replaced by the small fraction of cells which divide, and population constancy is maintained. Below $HEM_{84}$, total cell division exceeds cell death; while above $HEM_{84}$ all cell division is blocked and population decrease gradually occurs due to cell death. The relatively rapid decrease in viable cells in $HEM_{89}$ indicates that the condition of this $E_m$ level, or at least the abrupt imposition of this level, on cells may be relatively toxic. To insure complete mitotic blockage in the ensuing test, $HEM_{85}$ was taken as the minimum $E_m$ for mitotic arrest.

Figure 3:
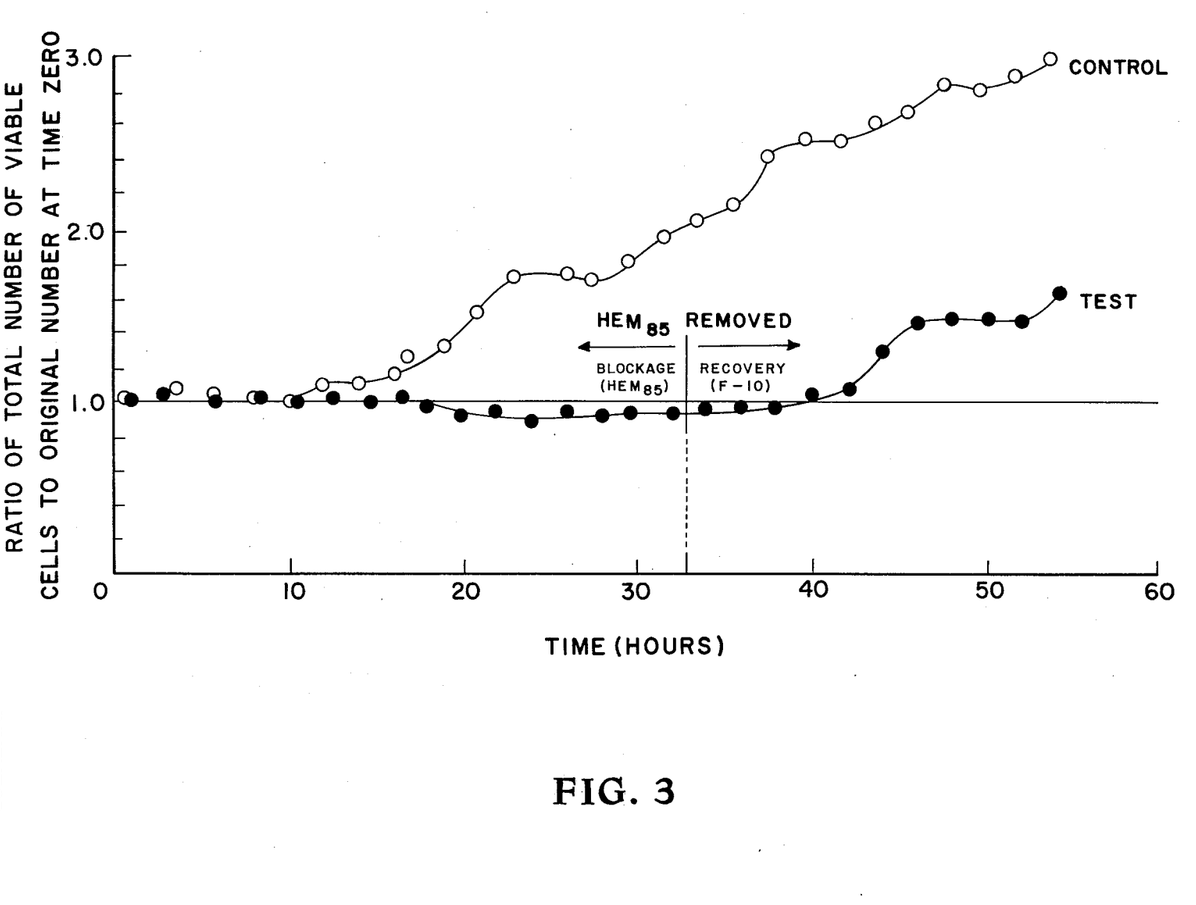
FIG. 3 is a graph showing the effect of a simulated $E_m$ level of −70mV ($HEM_{85}$ test medium) on mitotic activity in naturally synchronized somatic cells; control cells maintained in normal F-10 medium; $HEM_{85}$ test medium was replaced with F-10 medium at 32.8 hours.

The effect of $HEM_{85}$ medium on cell mitotic activity is shown in FIG. 3. (Example III) As expected from the preliminary tests, $HEM_{85}$ entirely blocks cell division during the 33-hour treatment, whereas the control cells in normal F-10 proceed to divide in a synchronous wave with a cycle time of 2 hours. Direct visual observation again demonstrated no cell death beyond control values during the 33-hour blockage period. The data of this figure demonstrate that the $E_m$ induced mitotic blockage is fully reversible; the midpoint of the mitotic rise occurs some 11 hours after removal of the $HEM_{85}$. A percentage of the previously blocked cells which divide was essentially the same as for the first mitotic wave of the unblocked controls.

Figure 4:
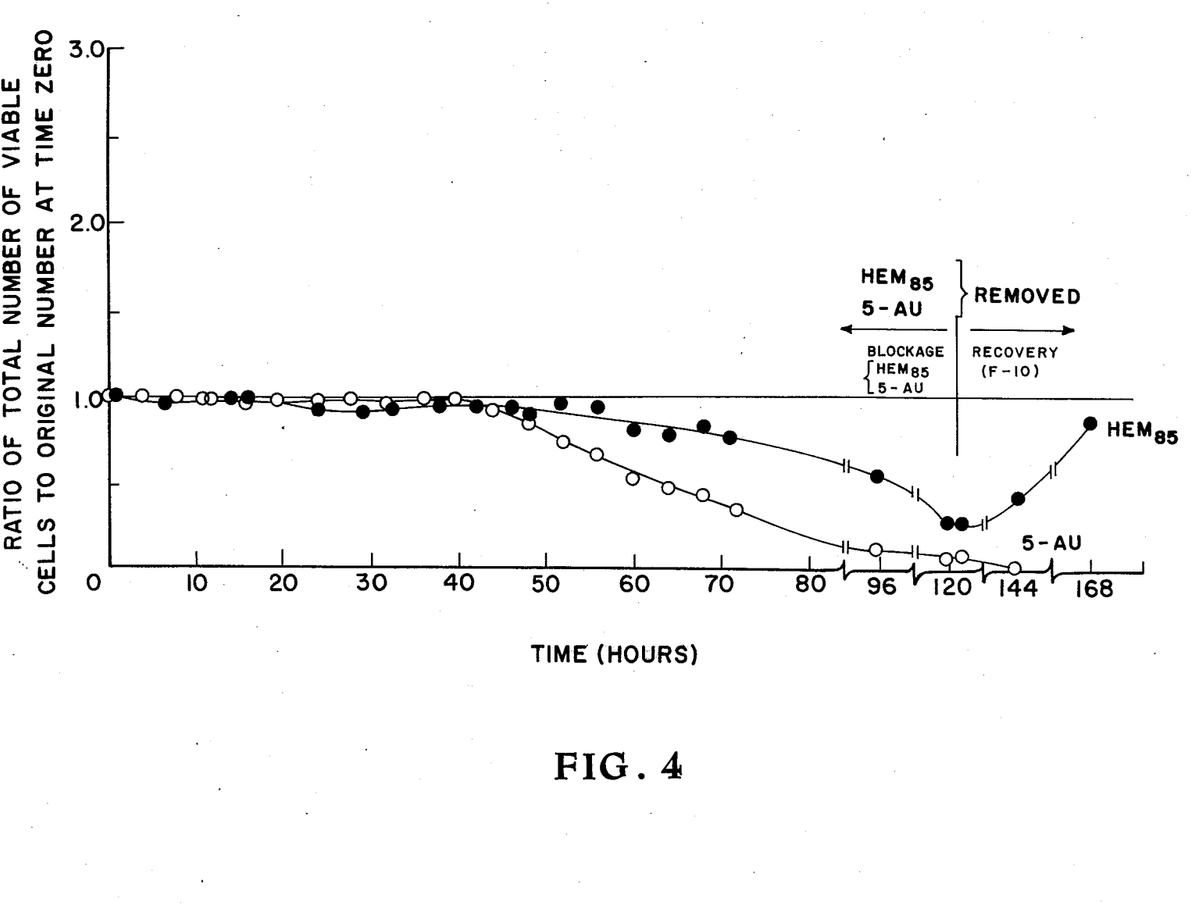
FIG. 4 is a graph showing compartive long-term effects of continuous simulated $E_m$ level of −70mV ($HEM_{85}$ test medium) and treatment with 5-aminouracil (0.4 mg/ml) on mitotic activity and cell death on naturally synchronized somatic cells; test media replaced with F-10 medium at 120.6 hours, F-10 medium used on control cells, as in FIG. 2.

The results of tests to ascertain the long-term blocking effect of $HEM_{85}$ are shown in FIG. 4 (Example IV). It is seen that mitosis is in fact completely blocked so long as the cells are maintained at the high $E_m$ level, as determined by direct visual observation over the 120-hour period. The percentage of dead cells increased very slowly up to 60 hours (3T), following which the death rate began to increase. At $t = 120$ hours (6T), some 26 percent of the initial population were still viable and morphologically normal in appearance except for slight rounding. Following replacement of the test medium, mitotic activity resumed in the remaining cells, such that 40 percent had divided within 26 hours. Also shown in FIG. 4 are the results of the comparison of long-term mitotic blockage tests in which 5-aminouracil (5-AU) was used as the blocking agent (Example V). The 5-AU concentration used was the minimum required for blocking all mitosis in cells maintained in F-10 -as determined by separate tests. As is evident, long-term cell death with 5-AU appreciably exceeds that with $HEM_{85}$, beyond 50 hours. In addition, the 5-AU blocked cells underwent grotesque morphological changes into multinucleate giant cells; these cells subsequently died without division following replacement of the 5-AU test medium with normal F-10. Thus, while the cell death rates during long-term mitotic blockage with $HEM_{85}$ and 5-AU are roughly comparable, such mitotic blockage is reversible only in the case of the $HEM_{85}$.

Figure 5:
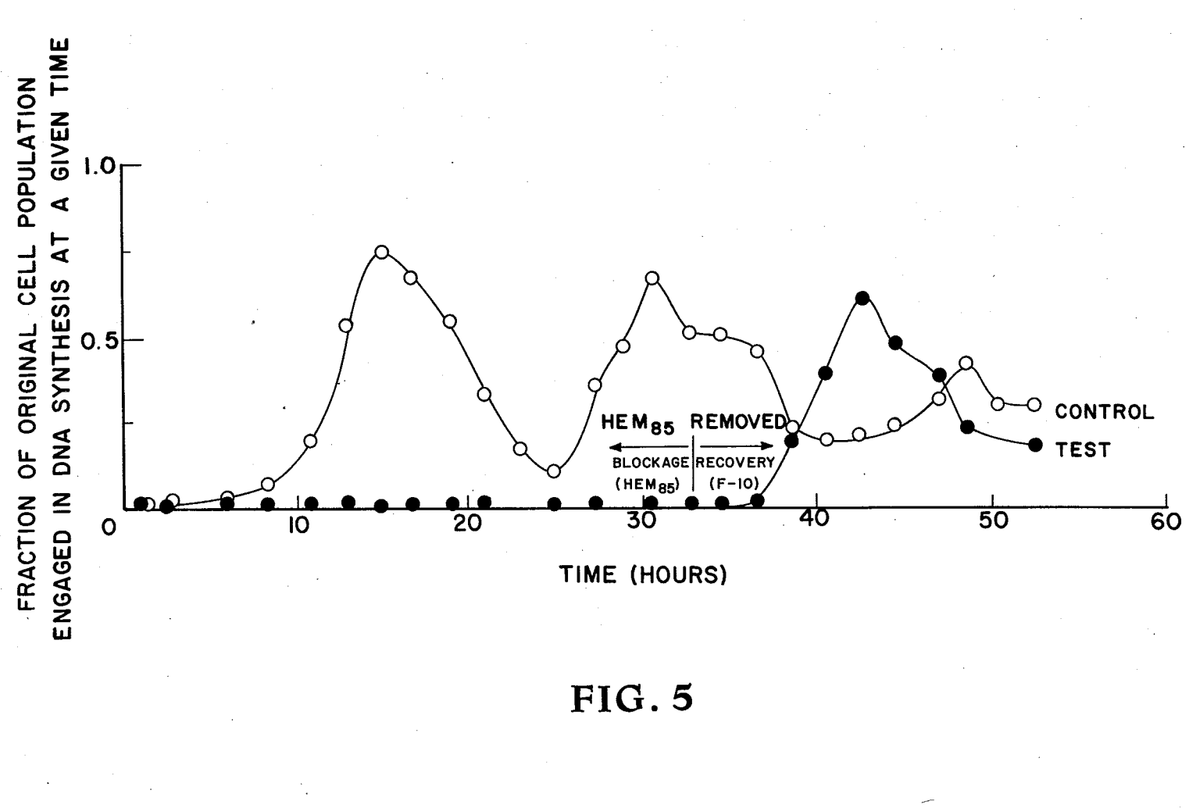
FIG. 5 is a graph showing the effect of a simulated $E_m$ level of −70mV ($HEM_{85}$ test medium) on DNA synthesis activity in naturally synchronized cells as determined by $^3$H-thymidine pulse labelling; control cells maintained in normal F-10 medium.

The reversibility of HEM-blocked cells was further demonstrated by an additional experiment in which unsynchronized cells were maintained in $HEM_{89}$ for approximately 168 hours ($\sim 8.5T$). The effect of $HEM_{85}$ on DNA synthesis in cells is shown in FIG. 5 (Example VI), this data corresponding to the mitotic blockage and recovery test results presented in FIG. 3 with the test cells coming from the same original population. The data clearly demonstrate that the simulated high $E_m$ level corresponding to $HEM_{85}$ fully (but reversibly) blocks DNA synthesis, and thus implies that the mitotic blockage shown in FIG. 3 is a consequence of the prior blockage of DNA synthesis. From FIG. 5, the time required for attainment for maximum DNA synthesis activity in F-10 (control cultures) is 15 hours. This is essentially the combined lengths of the $G_1$ (7.5 hour) and S (7.0 hour) periods for cells with a 20 hour cycle period. Assuming that the DNA synthesis of the $HEM_{85}$ blocked cells is also 7 hours (as seems reasonable from the data), then it appears that $G_1$ mitotic blockage occurs at a point roughly 3 hours before the end of the $G_1$ period, since maximum DNA synthesis activity occurs some 10 hours after removal of the $HEM_{85}$. Thus, if no appreciable time is required for recovery and resumption of mitotically directed metabolism after removal of the $HEM_{85}$, mitotic blockage by $HEM_{85}$ apparently occurs late in the $G_1$ period. The autoradiographic studies of DNA synthesis conducted as part of the long-term test (FIG. 4) revealed, as might be expected, the complete absence of DNA synthesis during the treatment period.

One series of short-time (33-hour) blockage tests was run using cells in suspension (spinner culture) with electronic counting. These tests yielded essentially the same DNA and mitosis blockage and recovery effects as observed with the monolayer cells only the cycle period was slightly longer.

ALTERNATES

Generally, it is desirable to reproduce as closely as possible the actual intracellular concentration hierarchy of $Na^+$, $K^+$, and $Cl^-$ in order to simulate as nearly as possible the ionic hierarchy which accompanies naturally attained high and low $E_m$ levels. It has been found in practice that the really essentially ion is $Na^+$. The $K^+$ and $Cl^-$ concentrations may vary substantially from their usual physiological values at high and low $E_m$ levels without noticeable effect on mitogenesis. Thus, so long as the $Na^+$ concentration is properly modulated, simulation of the concentration of the remaining ions of the inorganic ion hierarchy is not critical to mitogenesis and may be varied over a substantial range. Furthermore, the exact $Na^+$ concentration is not of critical importance (within reasonable limits), so long as its value lies below the critical threshold level required to block DNA synthesis and mitosis, and well above this level for the stimulation of DNA synthesis and mitosis. The $Na^+$ concentration level can be precisely stated for cells. However, since intracellular $K^+$ and $Cl^+$ levels and the actual level of $Na^+$ may affect other aspects of cellular metabolism besides those associated specifically with mitosis, it is considered desirable to approximate the natural intracellular ionic concentration hierarchy of high and low $E_m$ concentrations as closely as possible to secure the full benefits of the process in regard to nondisturbance of normal celular metabolism when inducing mitosis control by means of the present process.

SUMMARY

From the above description of the invention, the many advantages thereof are believed to be apparent. The present invention is believed to be patterned after nature's own mechanism of mitotic control, by providing a natural, reversible means for obtaining mitotic regulation for various applications. Since the blockage of division is reversible, indigent cells whose mitosis is also blocked during a particular application suffer no harm and resume division upon removal of the blocking ionic hierarchy (i.e., by the imposed or simulated high $E_m$ levels). Since in the present process, the blockage of mitosis proceeds by relatively natural means, normal metabolic functions of the cells are not upset. Since the $E_m$ level (and associated intracellular ionic hierarchy) of cells is intimately associated with their surface characteristics, and the cell surface is the site of inmunological specificity, the present process offers a potential means whereby mitotic blockage or assimulation of particular cell populations can be achieved.

What is claimed as new and desired to be secured by Letters Patent of the United States is:

1. A reversible process for controlling division of biological cells which consists essentially of
    adjusting the effective cellular electrical transmembrane potential difference to a desired level between about −10mV and about −90mV by varying the relative intracellular concentrations of $Na^+$, $K^+$ and $Cl^-$ ions,
    maintaining the thus imposed transmembrane potential difference at a constant level for a time sufficient to permit the cell metabolism to stabilize at the imposed level of transmembrane potential difference, and
    further maintaining the imposed transmembrane potential difference at a constant level for an additional time sufficient to achieve the desired cellular effect.

2. The process of claim 4 wherein division of biological cells is blocked by varying the relative intracellular concentrations of said ions so as to induce and maintain an effective cellular electrical transmembrane potential in the range of from about −70mV to about −90mV.

3. The process of claim 2 wherein the biological cells are naturally synchronized mammalian somatic cells.

4. The process of claim 1 wherein division of biological cells is actively stimulated by varying the relative intracellular concentrations of said ions so as to induce and maintain an effective cellular electrical transmembrane potential difference in the range of from about −10mV to about −20mV.

5. The process of claim 4 wherein the biological cells are naturally synchronized mammalian somatic cells.

6. The process of claim 1 wherein division of biological cells is first blocked by varying the relative intracellular concentrations of said ions so as to induce and maintain an effective cellular electrical transmembrane potential difference in the range of from about −70mV to about −90mV and after a time sufficient to achieve the desired degree of blockage, varying the relative intracellular concentrations of said ions so as to induce and maintain an effective cellular electrical transmembrane potential difference in the range of from about −10mV to about −20mV, thereby removing the block and actively stimulating division of biological cells.

7. The process of claim 1 wherein division of biological cells is first actively stimulated by varying the relative intracellular concentrations of said ions so as to induce and maintain an effective cellular electrical transmembrane potential difference in the range of from about −10mV to about −20mV and after a time sufficient to achieve the desired degree of stimulation, blocking the further division of biological cells by varying the relative intracellular concentrations of said ions so as to induce and maintain an effective cellular electrical transmembrane potential difference in the range of from about −70mV to about −90mV.

8. The process of claim 1 effected solely by directly varying the $Na^+$ concentration, thereby effectively varying the relative intracellular concentrations of Na$^+$, K$^+$ and Cl$^-$.

9. The process of claim 1 effected by surrounding the cells with an isotonic solution of Na$^+$, K$^+$ and Cl$^-$ ions wherein the relative concentrations of said ions differ from those normally surroundng the cells.

10. The process of claim 1 wherein the relative intracellular concentrations of said ions are indirectly varied by changing the surface ionic permeability of the cells.

UNITED STATES PATENT OFFICE
CERTIFICATE OF CORRECTION

Patent No. 4,018,649            Dated April 19, 1977

Inventor(s) Clarence D. Cone, Jr.

It is certified that error appears in the above-identified patent and that said Letters Patent are hereby corrected as shown below:

The cover sheet of the patent in section [73] should state:

Assignee: The United States of America as represented by the Administrator of the National Aeronautics and Space Administration, Washington, D. C.

Signed and Sealed this second Day of August 1977

[SEAL]

Attest:

RUTH C. MASON
*Attesting Officer*

C. MARSHALL DANN
*Commissioner of Patents and Trademarks*